United States Patent [19]

Saltzman

[11] 3,931,256

[45] Jan. 6, 1976

[54] CHEMICAL PROCESS FOR PRODUCTION OF BILE ACIDS

[75] Inventor: William H. Saltzman, New Rochelle, N.Y.

[73] Assignee: Intellectual Property Development Corporation, New Rochelle, N.Y.

[22] Filed: Feb. 6, 1975

[21] Appl. No.: 547,854

Related U.S. Application Data

[63] Continuation of Ser. No. 417,170, Nov. 19, 1973, which is a continuation-in-part of Ser. No. 290,960, Sept. 21, 1972, abandoned.

[52] U.S. Cl. ............................................. 260/397.1
[51] Int. Cl.² ........................................... C07J 9/00
[58] Field of Search ................................. 260/397.1

[56] References Cited

UNITED STATES PATENTS 3,846,411  11/1974  Widaver et al. ................. 260/397.1

FOREIGN PATENTS OR APPLICATIONS 990,120  4/1965  United Kingdom ............. 260/397.1

Primary Examiner—Elbert L. Roberts

[57] ABSTRACT

This invention relates to new and novel methods for the production of substantially pure bile acids, and particularly, 3α,7α-dihydroxy 5β-cholanic acid, from natural sources thereof.

9 Claims, No Drawings

CHEMICAL PROCESS FOR PRODUCTION OF BILE ACIDS

This application is a continuation application of my copending previously filed application Ser. No. 417,170, filed Nov. 19, 1973, which in turn is a continuation in part application of my prior filed application Ser. No. 290,960, filed Sept. 21, 1972, and now abandoned.

This invention relates to and has as its object, the production of substantially pure bile acids from natural sources thereof, and to new and useful processes therefore.

More particularly, this invention relates to new and novel methods for producing substantially pure bile acids, and particularly $3\alpha,7\alpha$-dihydroxy-$5\beta$-cholanic acid, from natural animal sources thereof. Bile acids are naturally occurring steroidal compounds, which are naturally synthesized by various animals. The most common of these natural bile acids are those possessing the following structure:

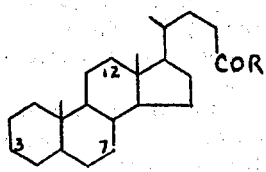

wherein R is a carboxyl group and hydroxyl substituents may be found in the 3,7 and/or 12 positions, depending on the particular bile acid involved.

In nature, bile acids are synthesized in the liver of animals and are incorporated into the bile, which is a fluid secreted by the liver and poured into the intestine of the animal. The bile acids are the major constituent of the bile and are usually produced in various numbers and quantities by different animals, all of which are incorporated into the bile. Among the common animal originated bile acids may be included: $3\alpha,7\alpha$-dihydroxy-$5\beta$-cholanic acid; $3\alpha,7\alpha,12\alpha$-trihydroxy-$5\beta$-cholanic acid; and $3\alpha,12\alpha$-dihydroxy-$5\beta$-cholanic acid.

Due to the fact that the animal incorporates all these bile acids and a number of other materials, for example, pigments, lipids and protein materials, into the bile, it has heretofore, been inconvenient and uneconomical to isolate any particular bile acid from animal bile and therefore, many individual bile acids, even though naturally occurring in some abundance, had to be prepared synthetically from various precursors. In addition, heretofore, it has not been possible to produce certain bile acids in a sufficiently pure form for various uses, for example medical therapy.

I have now discovered a method whereby individual bile acids, in substantially pure form, can be produced economically and efficiently, directly from natural animal bile. Most importantly, for purposes of this invention, I have discovered an economically efficient method for producing substantially pure $3\alpha,7\alpha$-dihydroxy-$5\beta$-cholanic acid from animal bile. The use of the term, "substantially pure", in this Specification and the Claims appended thereto, is meant to denote a chemical purity in excess of 99.0%, as evidenced by standard and acceptable analytical procedures. Heretofore, it has not been possible to produce substantially pure bile acids directly from natural animal bile.

The animals which may be employed as the source of natural animal bile in the practice of this invention, are those whose bile is rich in the desired bile acid. Among those animals which may be included in this group are such animals as birds, for example, chickens, turkeys, geese, pheasants, owls and ducks; mammals, for example, oxen, rats, guinea pigs, bears and pigs; and fish, for example, cod fish, mullet fish, anchovies and harder fish. The most preferred source of the natural bile are animals, the major constituent of whose bile is the desired dihydroxy bile acid, and these include such birds as chickens, turkeys, geese and ducks. The process of this invention involves a number of steps commencing with a suitable animal bile as starting material. The animal bile, for example chicken or turkey bile, may be collected in any manner known to and convenient to the skilled worker, with the usual precautions being taken to avoid damage or deterioration of the animal bile starting material.

The successful practice of this invention involves two major procedures in the treatment of the natural animal bile to obtain the desired substantially pure bile acid. The first of these major procedures involves the removal from the natural animal bile of the undesired impurities and other extraneous materials, such as pigments, lipids and protein substances found therein. The second major procedure involves the isolation and purification of the desired bile acid, after all the undesired impurities have been removed.

REMOVAL OF IMPURITIES FROM NATURAL ANIMAL BILE

The removal of the undesirable impurities from natural animal bile including bile pigments, lipid impurities and the like, can be achieved by a number of new and novel procedures. One such method involves the direct solvent extraction of these impurities with an organic solvent capable of solubilizing the bile acids in the bile, and in which solvent the impurities are insoluble, for example, an alcohol, such as methanol or ethanol; a ketone, such as acetone; or an acid, such as, acetic acid; and other like solvents. The undesired impurities, due to their insolubility in the solvent, are caused to precipitate out of the solution and may then be removed by simple filtration. Although this method has given somewhat satisfactory results, it has been found that its practice does not remove substantially all the impurities and further purification is required to obtain removal of substantially all of the undesired material from the bile.

Another method to remove the unwanted impurities requires the natural bile to first be mildly hydrolyzed as by treatment with a base, such as an alkali metal base, for example, sodium hydroxide or potassium hydroxide. The hydrolyzed material is then neutralized and extracted with a suitable solvent system, for example, chloroform: methanol, in which the bile acids portion of the bile is soluble in one solvent, but the impurities are not, thus causing the impurities to be separated out into one solvent of the system and thus, rendering them subject to withdrawal therewith. This method, although more satisfactory than that set forth hereinabove, is also not capable of the removal of all of the impurities from the natural bile and additional purification is required to obtain the optimum final products of this invention.

Still another method that has been found to remove the impurities from the natural bile may be employed in the practice of this invention. This method involves first, mildly hydrolyzing the crude natural bile with a base, such as an alkali metal base, for example, NaOH or KOH, neutralizing the resultant hydrolyzed solution, and then dehydrating said solution, as by spray drying, lyophilization, drum drying, membrane separation or freeze drying. Although the hydrolysis procedure may be helpful in the removal of certain of the impurities, in certain cases, for example in chicken or turkey bile, I have found that the hydrolysis procedure can be dispensed with, and the natural animal bile is dehydrated as the first step in the process. By omitting the hydrolysis procedure in these instances, I have found that the quality and character of the final product is not adversely effected.

In the most preferred process of this invention, the natural crude animal bile is first dehydrated by any of the well known methods, such as those enumerated above. It is preferred that the dehydration procedure be accomplished by freeze drying, or lyophilization, although the other well known methods also yield equivalently satisfactory results.

The resultant dehydrated natural bile material is then esterified as by treatment with a suitable esterification agent. Depending upon the animal which is the source of the natural bile, the esterification agent employable in the practice of this invention, may be altered. Preferably, the esterification agent employed in this invention is an alcohol, which may be a hydrocarbon alcohol or may be a substituted alcohol. Among the alcohols which may be employed as esterification agents herein may be included such saturated or unsaturated alcohols as the alkanols, for example, methanol, propanol or butanol; the alkenols, for example, ethenol, or propenol; the cyclic alcohols, for example, cyclohexanol, or cyclooctanol; the aryl alcohols, for example, phenol, benzyl alcohol, cinnamyl alcohol, and other like alcohol esterification agents. In addition, the alcohols of this invention may be substituted or unsubstituted and may contain such substituents as halides, for example, chlorides or bromides, or sulfur, or oxygen, without departing from the practice of this invention. Most preferably, I have found that esterification of the natural bile material may be satisfactorily accomplished by treatment thereof with an alkyl esterification agent, such as a methyl esterification agent, for example, methanol in an acid medium, such as a mineral acid, for instance, sulfuric acid. Where an alkyl esterification agent is employable in the practice of this invention, other alkylating agents may also be employed. Thus, such alkylating agents as diazomethane, may also be employed in the practice of this invention.

The esterification of the natural bile material yields the esters, for example the alkyl esters, of the bile material impurities, such as pigments, etc., whereupon they are apparently rendered soluble in certain organic solvents and insoluble in others. Likewise, the bile acids present in the bile are soluble in certain solvents and not in others. By subjecting the resultant esterified composition to the proper solvent system, it has been found to be possible to separate the bile acids from the impurities. Among the satisfactory solvent systems which may be employed in the practice of this invention are the halogenated hydrocarbon organic solvents such as chloroform, methylene chloride, methylene dichloride, such aromatic organic solvents such as, benzene, toluene, and the like, and such organic solvents as alcohols, for example, methanol and ethanol, alkanes, such as hexane or heptane, ketones, for example, benzophenone, or cyclohexanone, ethers, such as methyl or ethyl ether, carboxylic acids, for example, acetic acid, and other similar suitable organic solvents. In the practice of this invention, it has been found that a satisfactory solvent system is one which is comprised of at least two phases, in one phase of which the bile impurities are soluble and the remaining phases in which the said impurities are insoluble. Conversely, the desired bile acid fraction of the bile must be insoluble in the phase in which the impurities are soluble, while being soluble in the remaining phase. I have now found that a solvent system comprised of the following phases may be satisfactorily employed in the practice of this invention: halogenated hydrocarbon:alcohol, for example, chloroform:methanol, chloroform:ethanol, methylene chloride:methanol; aroamtic organic solvent:alcohol, for example, toluene:methanol, benzene:methanol; aromatic organic solvent:alkane, for example, benzene:hexane, toluene:hexane; ether:alcohol, for example, methyl ether:methanol; halogenated hydrocarbon:ketone, for example, chloroform:acetone; and other like organic solvent systems which the skilled worker may determine to be employable in the practice of the instant invention in conformance with the teachings set forth herein.

It has been found that the most economically satisfactory results may be obtained in the practice of this invention when the solvent system employed is comprised of a halogenated hydrocarbon phase and an alcohol phase. More particularly, a solvent system comprised of a halogenated hydrocarbon, for example, chloroform, and an alcohol, for example methanol, has provided very satisfactory results in the practice of this invention. The bile acid fraction of the crude bile is not soluble in the halogenated hydrocarbon solvent phase, while it has been unexpectedly been found that substantially all the esterified impurities are. It has also been found that for the most successful practice of this invention, it is desirable to process the dehydrated bile material under substantially anhydrous conditions. It appears that the presence of material amounts of water, either in the bile material or in the subsequent processing thereof results in a product of relatively unsatisfactory quality.

The vigorous admixing of the solvents and the bile, and the addition of a separating phase to the system, if desired, results in completely separated phases, one containing the undesired impurities and the other containing the bile acid fraction. Among those materials which may be employed as a separating phase, if one is desired, may be included dilute mineral acids, for example, hydrochloric or sulfuric acids, or water. Thus, all the impurities which are found in one solvent phase may be drawn off therewith, leaving only the bile acid solution, free of impurities, to further purify hereunder. This method of removal of the undesired impurities from the natural bile is the most preferred in the practice of this invention, and has been found to result in the most satisfactory final products hereunder. In practice, I have found that while the impurity containing solvent phase has a deep greenish, or greenish-black color, the bile acid containing solvent phase is almost water-white, and contains practically no detectable amounts of undesired impurities, such as pigments.

In nature, natural animal bile exists in a peptide conjugated form, i.e. the natural acids have, by the animal system, been conjugated with amino acids. The two principal amino acids with which the natural animal bile acids have been conjugated are glycine and taurine. In the case of the glycine conjugated bile acids, it has been found that a slight variation in the process by which the impurities and pigments are removed from the natural bile, as set forth hereinabove, can also provide satisfactory results. I have found an additional procedure whereby substantially all of the pigments and other undesired impurities in glycine conjugated bile can be removed, all without departing from the ambit of the instant invention.

The natural bile is brought to substantial dryness and esterified as aforesaid. However, the esterification is permitted to continue until and to the extent that the pigment fraction, the other impurity fraction and the bile acid fraction of the natural bile are all obtained in their esterified form. The esterification agents enumerated hereinabove may also be employed in the instant procedure. The thus completely esterified natural bile is then subjected to a selective hydrolysis reaction, wherein only the esterified bile acid fraction of the natural bile has been hydrolyzed. This selective hydrolysis may be accomplished by subjecting the esterified bile to the commonly employed hydrolysis procedures in the presence of a suitable pH adjusting buffer. It has been found that this selective hydrolsis procedure may be effectively carried out where the hydrolysis reaction mixture's pH is kept either highly basic, or highly acidic, for example, a pH of about 9–12, or about 1–3, respectively, the conditions of hydrolysis being adjusted accordingly, as is well known to the skilled worker. The selective hydrolysis reaction is continued until the esterified bile acid fraction of the bile is hydrolyzed to the free acids, and the resultant hydrolyzed bile is then subjected to the solvent separation procedure as set forth hereinabove, to yield the desired solvent phase containing the substantially pigment and impurity-free bile acid fraction of the natural bile. The solvent phase containing the bile acids may then be further treated by the processes of this invention to yield the desired final products thereof. The bile acid containing soltion may thus be neutralized, and the solvent evaporated off to yield a crude bile acid composition which may then be further treated hereunder.

ISOLATION AND PURIFICATION OF THE DESIRED BILE ACID

The crude bile acid composition thus obtained, may then be treated to obtain the desired final pure bile acid of this invention. One method that may be employed involves the hydrolysis of the crude bile acid composition to split off the amino acid conjugates, if any, in which form the naturally occurring bile acids are found. This hydrolysis may be accomplished by treating the bile acid composition with a hydrolyzing agent, for example an alkali metal base, such as KOH or NaOH. The resultant hydrolyzed material may then be acidified as by treatment with a mineral acid, such as HCl or $H_2SO_4$, and the acidified solution extracted with a suitable organic solvent, such as ethyl acetate, ethyl ether, isopropyl ether, or diisopropyl ether, and the resultant solution is reduced to dryness to yield a crude residue of the free bile cids.

This crude residue may then be esterified by treatment with a suitable esterification agent. Preferably, the esterification agent employed is one which will yield an alkyl esterified product, and may be an alcohol which is a hydrocarbon alcohol, which may be substituted or unsubstituted. Among the alcohols which have been found to provide satisfactory results hereunder, may be included such saturated or unsaturated alcohols as the alkanols, for example, methanol, propanol or butanol; the alkenols, for example, propenol; the cycloalkanols, for example, cyclohexanol; the aryl alcohols, for example, phenol, benzyl alcohol, cinnamyl alcohol, and other like alcohols. In addition, the alcohols employed herein may be substituted or unsubstituted and therefore, may contain such molecular substituents as halogens, for example, chlorine or bromine, or sulfur, without altering the satisfactory results obtained hereunder. In addition, further esterification agents may be employed in the practice of the foregoing procedure, particularly in the case where the objective thereof is the alkyl esterification of the substrate. Thus, such alkyl esterification agents such as diazomethane, and other like known agents may also be successfully employed in the practice of this invention.

Most preferably, in the practice of this invention, the crude residue obtained above, is subjected to alkyl esterification although the other esters thereof may also be employed herein.

This crude residue is then alkyl esterified as by treatment with an alkyl esterification agent, such as methanol in an acidic medium, for example, sulfuric acid, or diazomethane in ether, to yield the alkyl esters of the bile acids. These alkyl esters may then be subjected to colum nar extraction, for example in a column of alumina, employing a suitable solvent system, such as ethyl acetate-benzene, to yield the crude alkyl ester of the desired bile acid, i.e., $3\alpha,7\alpha$-dihydroxy-$5\beta$-cholanic acid. On further elution with a suitable solvent system, for example, methanol-ethyl acetate, additional crude alkyl ester of the $3\alpha,7\alpha$-dihydroxy-$5\beta$-cholanic acid, combined in the case of the bile source being chicken or turkey bile, with the alkyl ester of $3\alpha,7\alpha,12\alpha$-trihydroxy-$5\beta$-cholanic acid. The second eluate may then be recycled through the extraction column and with the proper solvent system, for example, ethyl acetate-benzene, yield further amounts of the crude alkyl ester of $3\alpha,7\alpha$-dihydroxy-$5\beta$-cholanic acid.

The reusltant crude alkyl ester of the desired bile acid is then hydrolyzed, as by treatment with a suitable base, for example an alkali metal base, such as, KOH or NaOH, and the resultant product acidified, extracted with a suitable solvent, filtered and dried. The resultant residue is then treated with a suitable solvent, such as ethyl acetate, at elevated temperature, and the reusltant solution, upon cooling, is found to contain substantially pure crystallised $3\alpha,7\alpha$-dihydroxy-$5\beta$-cholanic acid, which can be recovered by filtration.

Still another method has been found for obtaining substantially pure bile acids hereunder. After hydrolysis of the impurity free residue obtained as set forth hereinabove, to obtain the crude residue of free bile acids, this crude bile acid residue can be processed by a method whereby there is obtained a selective insoluble salt precipitation of the bile acid to yield the desired bile acid directly.

After removal of the impurities and the hydrolysis of the peptide conjugated bile acids, the resultant solution containing the free bile acids is treated with a suitable salt, which will cause a selective, differential bile salt precipitation in a suitable solvent. In other words, a suitable salt must be employed which will cause the formation of free bile acid salts which will possess differential solubilities in a selected solvent. Thus, where the free bile acids are 3α,7α-dihydroxy-5β-cholanic acid and 3α,7α,12α-trihydroxy-5β-cholanic acid, as in chicken, turkey and goose biles, the suitable salt which may be employed is one which will cause the resultant bile acid salts to have differential solubility properties in a particular solvent. The salts which have now been found to be employable in the practice of this invention in clude such salts as Group IIa metal salts. The Group IIa metal salts which may be employed in the practice of this invention include such salts as barium, strontium and calcium salts, for example, Group IIa halide salts, such as the chloride salts, such as barium chloride, or Group IIa acetate salts, or Group IIa nitrate salts. The free bile acid composition is treated with the suitable Group IIa salt, for example barium chloride, first in an aqueous solution to form the bile acid salts and then in a suitable solvent in which one of the resultant bile salts is soluble, while the other is not. In the case of the bile acids derived from chicken bile or turkey bile hereunder, a barium chloride salt and an organic solvent, for example, an alcohol, such as methanol, may be employed. The desired bile acid salt is thus separated, and may then be treated with an acid, such as a mineral acid, for example, HCl, to dissociate the salt and obtain the desired substantially pure free bile acid product. The resultant substantially pure bile acid final product may then be further purified if desired, as by recrystallization from a suitable solvent, and then dried to yield the substantially pure, free bile acid final product of this invention.

In addition to the foregoing, various other suitable organic solvents in which the resultant Group 11a bile acid salts will have a differential solubility, thus enabling their separation, may be employed in the practice of this invention. The skilled worker can easily determine those organic solvents which may thus be employed in the practice of this invention, which include such organic solvents, as ethyl acetate, hexane, and acetic acid, among others, all of which may be satisfactorily employed herein.

Further to the foregoing, the concurrently produced bile acid salt, which is not separated and purified hereunder, which in the case of chicken bile is 3α,7α,12α-trihydroxy-5β-cholanic acid, may also be further purified and treated in accordance with well known procedures to yield its respective free bile acid. Once isolated in its free bile acid form, in the case of chicken bile, the 3α,7α,12α-trihydroxy-5β-cholanic acid thus obtained, may be further treated as by the method described by Feiser et al, in Volume 72, Journal of the American Chemical Society, page 5530, (1950), to yield additional amounts of the desired 3α,7α-dihydroxy-5β-cholanic acid. Although the foregoing general description of this invention has been somewhat limited to a discussion of the treatment thereunder of natural bile containing material amounts of 3α,7α-dihydroxy-5β-cholanic acid, it should be understood that the principles and practice thereof is not limited to such natural bile and is generally applicable to all natural bile. I have found that with merely minor modifications easily determinable by the skilled worker in view of the teachings and disclosures hereof, the process for removal of the undesired impurities contained in natural bile is generally applicable to all natural animal bile and hence the process of this invention may also be employed to separate and purify the naturally occurring bile acids contained in such natural animal bile as may be obtained from oxen, pig, possum, sheep, and man.

The practice of this invention with such natural bile starting materials, including the animals listed hereinabove, and such laboratory animals as rats, guinea pigs and the like, will result in equivalent satisfactory production of the requisite substantially pure bile acids of this invention.

I have found in the practice of this invention that the resultant substantially pure bile acid, and particularly, the 3α,7α-dihydroxy-5α-cholanic acid produced hereunder, are the purest bile acids I have seen. The purity which has been checked by thin layer chromatography, gas liquid chromatography and melting point, has been shown to be in excess of 99+% and the melting point appears to be higher than any found in the literature, thus indicating a final product of extraordinary purity. Obviously, in those applications where the compound may be employed for medical uses, purity of the product is of utmost concern.

The invention is more particularly described and set forth in the following Examples:

EXAMPLE I

Ten ml. of chicken gallbladder bile are added to 200 ml. of hot methanol with stirring. After cooling, the resultant precipitate was removed by filtration and the alcoholic solution evaporated to dryness at 60°C., in vacuo. The resultant dry residue was then dissolved in 25 ml. of 10% aqueous NaOH and the solution autoclaved at 14 lbs/sq.in. for 3 hours. The solution is then cooled in an ice bath, acidified to pH 1.0 with 4N HCl, and extracted 4 times with 50 ml. of ethyl acetate. The organic solvent fractions are washed with water to near neutrality and dried over $Na_2SO_4$. The organic phase is then filtered off and evaporated to dryness. The resultant material is then dissolved in 25 ml. of anhydrous methanol containing 2% conc. $H_2SO_4$, allowed to stand overnight and an equal volume of water is added. The resultant solution is then extracted 3 times with 50 ml. diethyl ether-benzene (2:1v/v) and the organic phases combined, washed with 5 ml. of water, 5 ml. of saturated $NaHCO_3$ and again 3 times with 5 ml. of water. The solution is dried over $Na_2SO_4$, filtered and evaporated to dryness. The resultant residue is then dissolved in 50 ml. ethyl acetate-benzene (1:9v/v) and placed on a column of alumina, grade III, 200 grams. The column is washed with 400 ml. ethyl acetate-benzene (3:7v/v) to remove colored impurities. The methyl ester of 3α,7α-dihydroxy-5β-cholanic acid is then removed from the column with 800 ml. ethyl acetate-benzene (4:6v/v), and the solvent evaporated off in air at 60°C. The resultant residue is then dissolved in 50 ml. of 5% KOH in methanol and heated to 60° C. for 1 hour. The resultant solution is cooled in an ice bath and acidified to pH 1.0 with 4N HCl. The resultant acidic solution is diluted with 100 ml. of water and extracted 4 times with 75 ml. of ethyl ether, and the etheral solution washed with water to pH 5.0, dried over $Na_2SO_4$, filtered and evaporated to dryness. The resultant residue is then dissolved in 30 ml. of hot ethyl acetate and allowed to stand at room temperature. Upon cooling, crystallization occurs, and after filtration on a Buchner filter, with suction, and drying overnight in vacuo, there is obtained 447 mg. of 3α7α-dihydroxy-5β-cholanic acid, melting at 142°–144°C., analyzed as pure material by thin layer chromatography using the upper phase of a solvent system, toluene-acetic acid-water, (5:5:1 v/v/v) and 50% $H_2SO_4$ in water as detecting agent, The yield was calculated at 54.7%.

EXAMPLE II 50 ml. of crude chicken gallbladder bile was lyophilized to dryness to yield a dry greenish-black powder. This material was then dissolved in 100 ml. of anhydrous methanol and the solution heated to near boiling. The hot solution was then filtered and the green precipitate washed with 10 ml. of hot anhydrous methanol and discarded. The methanol wash was combined with the original methanol solution, 2 ml. of conc. $H_2SO_4$ was added and the solution allowed to stand overnight at room temperature. The solution was then transferred to a separatory funnel containing 200 ml. of chloroform and 20 ml. of water, and the funnel shaken for 1 minute to permit separation of the phases. The lower chloroform layer was a dark greenish color and contained all the pigment and other impurities, while the upper alcoholic layer was water-white and contained the bile acid fraction. The chloroform layer was drawn off and discarded.

EXAMPLE III 50 ml. of crude chicken bile was lyophilized to dryness to yield a dry greenish-black powder. This material was then dissolved in 100 ml. of methanol and the solution heated to near boiling, and then filtered. The resultant greenish-black precipitate was discarded. The filtered methanol solution was then treated with 5 gm. of KOH added at room temperature, with stirring, and the resultant solution allowed to stand overnight and was then neutralized with conc. $H_2SO_4$ with stirring. After neutrality was reached, 2 ml. of conc. $H_2SO_4$ was added and the solution allowed to stand overnight at room temperature. The solution was then cooled in an ice bath with 20 ml. of ice water and a saturated solution of sodium bicarbonate was added dropwise until a pH of 8.0–9.0 was reached. The solution was then filtered and transferred to a separatory funnel containing 200 ml. of chloroform and 20 ml. of water and shaken for 2 minutes to permit separation of the resultant phases. The lower chloroform layer was greenish in color and contained the undesired pigment and lipid impurities, while the upper methanol layer was near water white and contained the bile acids.

EXAMPLE IV

Fifty ml. of native chicken gallbladder bile is stirred with 2 gm. of NaOH until dissolved and allowed to stand overnight. The resultant solution was then cooled in an ice bath and 4N HCl was added dropwise with stirring until the pH was below 2.0. An additional 1 ml. of conc. HCl was then added. To the resultant solution with stirring, was added dimethoxypropane at the rate of 9 ml. per 1 ml. of solution, at room temperature, and stirring was continued for one hour and the resultant solution allowed to stand overnight. Thereafter, the solution was cooled in an ice bath, 10 ml. of ice water was added, and then a saturated aqueous sodium bicarbonate solution was added until the pH became alkaline. The resultant solution was filtered and transferred to a separatory funnel containing 200 ml. of chloroform and shaken for one minute, after which the phases were allowed to separate. The lower chloroform phase contained the unwanted impurities and was drawn off and discarded. The upper, colorless phase contained the bile acids in aqueous methanol-acetone.

EXAMPLE V

The clear solution obtained in Example II above, was concentrated by distillation to remove most of the organic solvents. The residual aqueous solution containing peptide conjugated bile acids was diluted with water containing sufficient NaOH to result in 100 ml. of solution containing 10% NaOH. The resultant colorless alkaline solution was then autoclaved at 14 lb/sq. in. for 3 hours, and the resultant hydrolyzed solution cooled in an ice bath and acidified with 4N HCl, dropwise with stirring, to yield a light yellow gummy precipitate. The precipitate was filtered off, washed with water and then dissolved in 80 ml. of 10% aqueous ammonium hydroxide with stirring, and then heated to near boiling. To the stirring solution was added dropwise, 40 ml. of a 10% barium chloride solution, yielding a white crystalline precipitate. The precipitate was filtered off, washed with methanol and dried in vacuo at 60°C., yielding a crude barium salt of $3\alpha,7\alpha$-dihydroxy 5-$\beta$-cholanic acid, weighing 4.9 gm., which was then suspended in 100 ml. of ethyl acetate, 100 ml. of 3N HCl was then added and the three phase system shaken until the precipitate was dissolved. The ethyl acetate layer was separated, the aqueous acidic layer was washed with 50 ml. of ethyl acetate and the ethyl acetate aliquots combined. The combined ethyl acetate solution was washed to neutrality with water and dried over sodium sulfate, and the aqueous layers were discarded.

The ethyl acetate of the resultant solution was then evaporated off and the residue was dissolved in 100 ml. of methanol and 10 ml of a 10% barium chloride solution was added with stirring followed by 1 ml. of conc. ammonium hydroxide, added dropwise with stirring. The resultant solution was brought to boiling, and allowed to cool to room temperature and filtered.

The filtrate was tested for completeness of precipitation by the addition of an amount of barium chloride solution and any precipitate formed was treated as above, to yield additional precipitate which was then added to the original precipitate and the combined material was then washed with methanol and dried in vacuo at 60°C., yielding a crude barium salt of $3\alpha,7\alpha$-dihydroxy-5$\beta$-cholanic acid, weighing 4.1 gm.

The crude barium salt thus obtained, was then shaken with 100 ml of 3N HCl and 100 ml of ethyl acetate until complete dissolution was obtained. The phases were allowed to separate, the ethyl acetate phase was drawn off, the aqueous acidic phase washed with ethyl acetate and the ethyl acetate aliquots combined, washed to neutrality with water and dried over sodium sulfate. The aqueous layers were discarded.

The washed and dried ethyl acetate solution of $3\alpha,7\alpha$-dihydroxy-5$\beta$-cholanic acid thus obtained, was then evaporated to a volume of 40 ml. at 50°C. under a stream of air. The resultant solution was then cooled to 4°C. and n-hexane at 4°C. was added until the solution became slightly turbid. The ethyl acetate-n-hexane solution was then allowed to stand overnight at 4°C., causing pure $3\alpha,7\alpha$-dihydroxy-5$\beta$-cholanic acid to crystallize on the walls of the flask. The crystals were collected by filtration and washed with n-hexane, and dried in vacuo at 60° C. yielding 3.2 gm. of pure $3\alpha,7\alpha$-dihydroxy-5$\beta$-cholanic acid, (99.0% pure by gas liquid chromatography) having a melting point of 140°–142°C.

Further purification of the product may be obtained by following the procedures set forth in the succeeding Examples VI to IX.

EXAMPLE VI

The product obtained in Example V is dissolved in ethyl acetate to which n-hexane is added, and the solution is subjected to five plate countercurrent distribution between 25 ml. of 70% acetic acid (aqueous) and 40 ml. of 40% isopropyl ether in n-hexane v/v. The purified bile acid product will be in the isopropyl ether phase from which it may be recovered by evaporation.

EXAMPLE VII

The product obtained in Example V above, may be further purified by column partition chromatography on Celite columns containing 70% acetic acid as the stationary phase, 40% isopropyl ether-n-hexane as the mobile phase. A 100gm. column purifies 1 gm. of the crude bile acid.

EXAMPLE VIII

The product obtained in Example V above, may be further purified by adsorption chromatography on acidic alumina, activity grade V. The crude bile acid is dissolved in ethyl acetate or acetone and put through the column, which absorbs the impurities and allows the pure bile acid solution to pass through.

EXAMPLE IX

The crude bile acid product obtained in Example IV above, may be esterified with either diazomethane or methanol in $H_2SO_4$ as described in Example I above, and the esterified material purified on an alumina column as fully set forth in Example I, above.

EXAMPLE X

The procedure of Example V was followed to the point where 4.9 grams of dry crude barium salt of $3\alpha,7\alpha$-dihydroxy-$5\beta$-cholanic acid is obtained. To this dry crude material was then added 100 ml. of absolute methanol and the solution heated to near boiling with stirring, until the crude material completely dissolves. The heated solution was then cooled whereupon white crystals formed. The solution was filtered and dried to yield the barium salt of $3\alpha,7\alpha$-dihydroxy-$5\beta$-cholanic acid, weighing 4.0 gm. and more than 98% pure barium salt. The barium salt thus obtained was then shaken with 100 ml. of 3N HCl and 100 ml. of ethyl acetate until complete dissolution was obtained. The phases were allowed to separate, the ethyl acetate phase was drawn off, the aqueous acidic phase washed with ethyl acetate and the ethyl acetate aliquots combined, washed to neutrality with water and dried over sodium sulfate.

The washed and dried ethyl acetate solution was then evaporated to a volume of 45 ml. at 50°C. under a stream of air and the resultant solution cooled to about 4°C. and held there overnight, causing pure $3\alpha,7\alpha$-dihydroxy-$5\beta$-cholanic acid to crystallize. The crystals were collected and dried in vacuo to yield 3.1 gm. of pure $3\alpha,7\alpha$-dihydroxy-$5\beta$-cholanic acid, (99.0+% pure by gas liquid chromatography), having a melting point of 141°–143°C.

The foregoing procedure may also be successfully practiced with equivalent amounts of anhydrous ethanol, acetone or acetic acid being substituted for the absolute methanol solvent.

EXAMPLE XI

The procedure of Example V is followed, except that equivalent amounts of n-heptane or n-octane or n-pentane are substituted for the n-hexane yielding like results.

EXAMPLE XII

The procedure of Example II was followed except that natural anchovy, harder fish, codfish or sheep bile was substituted for the chicken gallbladder bile, yield a clear light colored solution which is substantially free from impurities and contains substantially all the bile acids of the respective bile.

EXAMPLE XIII

The method of Examples I, II, III, IV and V are followed except that turkey gallbladder bile, goose biles and duck bile are substituted for the chicken gallbladder bile, with equivalent results being obtained.

EXAMPLE XIV 50 ml. of crude hog bile was lyophilized to yield a light greenish-yellow powder. This material was then dissolved in an hydrous methanol, heated and filtered. Additional methanol was added and the methanol solution is then treated with sulfuric aciduntil complete esterification of the bile material is obtained. The esterified bile is then subjected to selective hydrolysis as by treatment with an alkali metal base at an elevated temperature, in the presence of an alkaline buffer whereby the pH of the reaction mixture is maintained at between 10 and 11. The hydrolysis reaction is allowed to continue until the bile acid fraction of the bile is hydrolyzed. The resultant selectively hydrolyzed bile is then transferred to a separatory funnel containing 200 ml. of chloroform and 20 ml. of water and the funnel shaken for 1 minute to permit phase separation. The lower chloroform phase is intensely greenish-yellow in color and contains substantially all the pigment and other impurities, while the upper alcoholic phase is a clear light yellow in color and contains the bile acid fraction of the bile. The chloroform layer is drawn off and discarded.

Following the procedure of Example V, but substituting the light yellow solution obtained above for the solution of Example II, there is obtained the desired free bile acid.

EXAMPLE XV

Following the procedure set forth in Example II, but substituting equivalent amounts of hexane, dimethyl ether, acetone or acetic acid for methanol, equivalent results may be obtained.

EXAMPLE XVI

Following the procedure set forth in Example II, but substituting equivalent amounts of toluene, methylene chloride, benzene or methylene dichloride, for chloroform. equivalent results are obtained.

The invention may variously otherwise embodied within the scope of the appended claims.

What is claimed is:

1. A method for the production of substantially pure bile acids from natural animal bile, which comprises:
    a. Extracting the naturally occurring bile acids from the natural animal bile by the treatment thereof with a multiphasic organic solvent system having at least two phase, in one phase of which the said bile acids are soluble and the naturally occurring pigments and impurities contained therein are not soluble, and in the remaining phases of which the said impurities and pigments are soluble and the said bile acids are not soluble;
b. Hydrolyzing the said extracted bile acids by treating with an alkali metal base;
c. Esterifying the resultant hydrolyzed bile acids by treating with an alcohol esterification agent;
d. Isolating the desired esterified bile acid; and
e. Recovering the resultant substantially pure free bile acid.

2. The method of removing bile pigments and other impurities from natural animal bile, which comprises:
a. Substantially dehydrating said natural animal bile;
b. Esterifying said substantially dehydrated natural animal bile by treatment with a suitable organic esterification agent;
c. Subjecting said esterified natural animal bile to a multiphasic organic solvent system having at least two phases in one phase of which the bile acid fraction of said animal bile is soluble and the pigments and other impurities thereof are not soluble, and in the remaining phases of which the said pigments and other impurities are soluble and the bile acid fraction is not soluble;
d. Separating and recovering the substantially pigment and impurity-free bile acid fraction of the natural animal bile.

3. The method of claim 2, wherein the natural animal bile is derived from birds.

4. The method of claim 2, wherein the natural animal bile is selected from the bile of chicken, turkeys, geese and ducks.

5. The method of claim 2, wherein the natural animal bile is chicken bile or turkey bile.

6. The method of claim 2, wherein in step c., the multiphasic organic solvent system is selected from the group consisting of halogenated hydrocarbon: alcohol; aromatic organic solvent: alcohol; aromatic organic solvent: alkane; ether: alcohol; and halogenated hydrocarbon: ketone.

7. The method of claim 2, wherein in step b., the organic esterification agent is an alcohol.

8. The method of claim 2, wherein in step b., the organic esterification agent is an alkyl esterification agent.

9. The method of claim 2, wherein the natural animal bile is chicken or turkey bile; wherein in step b., the organic esterification agent is an alkyl esterification agent; and wherein in step c., the multiphasic organic solvent system is halogenated hydrocarbon: alcohol.

* * * * *